United States Patent [19]

Kittelmann et al.

[11] Patent Number: 5,334,514
[45] Date of Patent: Aug. 2, 1994

[54] PROCESS FOR THE PRODUCTION OF ACTIVATED SIALIC ACIDS

[76] Inventors: Matthias Kittelmann, Kartäuserstrasse 88, 7800 Freiburg, Fed. Rep. of Germany; Oreste Ghisalba, Eschenweg 3, 4153 Reinach, Switzerland; Teresa Klein, Mariengartenstrasse 6, 5170 Jülich, Fed. Rep. of Germany; Udo Kragl, 665 Takarazuka-Shi, Takatsukasa-3-6-32 Nigawa, Greenheight 105, Japan; Christian Wandrey, Wolfshovener Strasse 139, 5170 Jülich, Fed. Rep. of Germany

[21] Appl. No.: 152,269

[22] Filed: Nov. 12, 1993

Related U.S. Application Data

[63] Continuation of Ser. No. 915,474, Jul. 16, 1992, abandoned.

[30] Foreign Application Priority Data

Jul. 17, 1991 [CH] Switzerland .................... 2119/91

[51] Int. Cl.$^5$ ............................................. C12P 19/26
[52] U.S. Cl. ....................................... 435/84; 435/89; 435/90; 435/91; 435/194
[58] Field of Search ................ 435/41, 89, 90, 91, 435/84, 194

[56] References Cited

FOREIGN PATENT DOCUMENTS 0120328 10/1984 European Pat. Off. .
3626915 2/1988 Fed. Rep. of Germany .
3937891 5/1991 Fed. Rep. of Germany .
63-334782 12/1988 Japan .

OTHER PUBLICATIONS

Chem. Abstr. 115:157140m (May 1991).
Chem. Abstr. 109:72046m (Feb. 1988).
Shames et al., Glycobiology vol. 1, No. 2, pp. 187–191 (1991).
Uchida et al., Agr. Biol. Chem. 37(9), 2105–2110 (1973).
Reuter et al., Proc. Jap. Germ. Symp. Sialic Acids (1988) 98–100.
Simon et al., J. Am. Chem. Soc. 110, 7159–7163 (1988).
Simon et al., Methods in Enzymology 179, 275–287 (1989).
Auge et al., Tetrahedron Lett., vol. 29, No. 7, 789–790 (1988).
Gross et al., Eur. J. Biochem. 168, 595–602 (1987).
Thiem et al., Liebigs Ann. Chem. (1990) 1101–1105.
Higa et al., J. Biol. Chem. 260, 8838–8849 (1985).
Vann et al., J. Biol. Chem. vol. 262, No. 36, 17556–17562 (Dec. 1987).
Warren et al., J. Biol. Chem. vol. 237, No. 11 (Nov. 1962) 3527–3534.
Ichikawa et al., J. Am. Chem. Soc. (1991) 113, 4698–4700.

*Primary Examiner*—Herbert J. Lilling
*Attorney, Agent, or Firm*—Karen G. Kaiser; Irving M. Fishman

[57] ABSTRACT

The invention relates to a process for the production of cytidine 5'-monophosphosialic acids which comprises reacting a sialic acid with cytidine 5'-triphosphate in the presence of a cell extract of a naturally occurring microorganism having cytidine 5'-monophospho-N-acetylneuraminic acid synthetase activity, the extract optionally having been subjected to one purification step.

15 Claims, No Drawings

PROCESS FOR THE PRODUCTION OF ACTIVATED SIALIC ACIDS

This is a continuation of application Ser. No. 07/915,474, filed Jul. 16, 1992 and now abandoned.

The invention relates to a novel process for the production of activated sialic acids, especially CMP-activated sialic acids, using microbial cell extracts.

Sialic acids, as essential components of glycoconjugates, such as glycoproteins and glycolipids, play a prominent role in a large number of biological processes. For example sialyl oligosaccharides exposed at the cell surface are receptor determinants for viruses, mycoplasms, plant and animal lectins, bacterial toxins, interferons and also certain tumour-specific and blood group-specific antibodies. In addition, terminal sialyl radicals often fulfil a masking function for the glycan radicals they terminate, so that the presence or absence of terminal sialyl radicals can have a decisive influence on the biological half-life of the glycoconjugate. For example, a considerably prolonged half-life can be achieved by enigmatically degrading the mannose-rich N-glycan chains of recombinant yeast proteins (for example recombinant t-PA from *S. cerevisiae*) and appending a terminal galactosyl-sialic acid group to proteins protected in such a manner.

Approximately 30 different naturally occurring sialic acids are known, with N-acetylneuraminic acid (Neu-5Ac) being the most important. As detailed studies have shown, the bio-synthesis of sialylated glycoconjugates is effected by way of nucleotide phosphate-activated sialic acids, especially cytidine 5'-monophosphate(CMP)-activated sialic acids, which are appended to the growing carbohydrate chain in the presence of specific sialyl transferases. Numerous methods of synthesising nucleotide phosphate-activated sialic acids, such as especially CMP-Neu5Ac, are known from the literature. For example Vann et al. (*J. Biol. Chem.* (1987) 262, 17556–17562) and Warren et al. (ibid. (1962) 237, 3527–3534) use enzyme preparations from *E. coli* and *N. meningitidis*, respectively, that have been subjected to several purification steps and contain the corresponding bacterial CMP-Neu5Ac synthetase, to prepare CMP-Neu5Ac from cytidine triphoshate (CTP) and Neu5Ac, whilst recently Ichikawa et al. (*J. Am. Chem. Soc.* (1991) 113, 4698–4700) and Shames et al. (*Glycobiology* (1991) Vol. 1, No. 2, 187–191) have used *E. coli*-CMP-Neu5Ac synthetase that has been prepared by recombinant genetic engineering methods and purified by antibody affinity chromatography or dyestuff ligand affinity chromatography. In the more customary processes, enzyme preparations of animal origin (e.g. pig, horse, calf, cattle, frog) are used to react CTP and Neu5Ac to form CMP-Neu5Ac, see, e.g., Higa et al. (*J. Biol. Chem.* (1985) 260, 8838–8849), Thiem et al. (*Liebigs Ann. Chem.* (1990), 1101–1105), Gross et al. (*Eur. J. Biochem.* (1987) 168, 595–602), German Offenlegungsschrift No. 3 626 915. In further processes known from the literature, the reactants CTP and/or Neu5Ac are also in some cases prepared in situ and further reacted in the presence of CMP-Neu5Ac synthetase to yield CMP-Neu5Ac, for example CTP is prepared from CMP and ATP, phosphoenolpyruvate or yeast cells that are able to convert CMP into CTP (see Simon et al. *J. Am. Chem. Soc.* (1988) 110, 7159–7163, Simon et al. *Methods Enzym.* (1989) 179, 275–287, Augé et al., *Tetrahedron Lett.* (1988) 29, 789–790, Japanese Laid-Open Specification No. 2 177 891), and Neu5Ac is prepared from N-acetylglucosamine or N-acetylmannosamine and pyrovale (see Simon et al. (1988, 1989), loc. cit.).

The known processes first of all have the disadvantage that complex and costly purification processes have to be employed to produce animal enzyme preparations and only extremely small amounts of CMP-Neu5Ac synthetase are present in cell homogenates of animal tissue, so that large volumes of biomass have to be worked up to obtain the enzyme in the amounts required for preparative purposes. Secondly, if animal tissue is used as the source of enzyme there is no guarantee that that source will always be available in large amounts and at a constantly high quality or that it will be free from viral contaminations that would place its use in question. A need therefore exists for novel processes for the preparation of CMP-Neu5Ac synthetase that make it possible to obtain that enzyme in any amount at a constantly high quality, especially without the disadvantages and risks attached to obtaining it from animal sources.

It has now surprisingly been found that it is possible to obtain from naturally occurring microorganisms having cytidine 5'-monophospho-N-acetylneuraminic acid synthetase activity (CMP-Neu5Ac synthetase) crude cell extracts that without further purification, or after only one preliminary purification step, catalyse the reaction of CTP with neuraminic acids to form the corresponding CMP-activated neuraminic acids. The cell extracts according to the invention are available in any desired amounts, since large volumes of biomass of constantly high enzyme activity can be obtained in a simple manner under standardised conditions by fermentation.

The invention accordingly relates to a process for the preparation of cytidine 5'-monophosphosialic acids which comprises reacting a sialic acid with cytidine 5'-triphosphate in the presence of a cell extract of a naturally occurring microorganism having cytidine 5'-monophospho-N-acetylneuraminic acid synthetase activity, the extract optionally having been subjected to one purification step.

Suitable sialic acids according to the present invention are, for example, those mentioned in Reuter et al. (Proceedings of the Japanese-German Symposium on Sialic Acids (1988), 98–100). The following sialic acids, especially, are suitable: N-acetylneuraminic acid (Neu5Ac), N-acetyl-4-O-acetylneuraminic acid (Neu4,5Ac$_2$), N-acetyl-9-O-acetylneuraminic acid (Neu5,9Ac$_2$), N-acetyl-7,9-di-O-acetylneuraminic acid (Neu5,7,9Ac$_3$), N-acetyl-8,9-di-O-acetylneuraminic acid (Neu5,8,9Ac$_3$), N-acetyl-9-O-lactoylneuraminic acid (Neu4Ac9Lt), N-acetyl-4-O-acetyl-9-O-lactoylneuraminic acid (Neu4,5Ac$_2$9Lt), N-acetylneuraminic acid 9-phosphate (Neu5Ac9P), N-glycoloylneuraminic acid (Neu5Gc), N-glycoloyl-9-O-acetylneuraminic acid (Neu9Ac5Gc), N-glycoloyl-9-O-lactoylneuraminic acid (Neu5Gc9Lt), N-glycoloylneuraminic acid 8-sulfate (Neu5Gc8S), and also 5-azidoneuraminic acid, N-acetyl-9-azido-9-deoxy-neuraminic acid and N-acetyl-9-acetamido-9-deoxy-neuraminic acid. Attention is drawn to Neu4,5Ac$_2$, Neu5,9Ac$_2$, Neu5Gc, Neu9Ac5Gc, N-acetyl-9-acetamido-9-deoxy-neuraminic acid, N-acetyl-9-azido-9-deoxyneuraminic acid, 5-azidoneuraminic acid and especially Neu5Ac.

The mentioned sialic acid compounds can be used as such in the reaction, or can be produced in situ in the reaction mixture from suitable precursors. For example Neu5Ac can be produced in situ from N-acetylmannosamine (Man2Ac) and pyruvate, it being necessary for a Neu5Ac aldolase also to be added to the reaction mixture. Furthermore, instead of using Neu5Ac in the reaction it is possible, for example, to use N-acetylglucosamine, which is converted in situ via Man2Ac into Neu5Ac using pyruvate in the presence of an N-acetyl-glucosamine epimerase and the mentioned aldolase.

Similarly, cytidine 5'-triphosphate (CTP) can be used in the reaction as such or in the form of a compound that can be converted into CTP. Suitable precursors are, for example, cytidine 5'-diphosphate (CDP) or especially cytidine 5'-monophosphate (CMP), which are converted into CTP by ATP or phosphoenolpyruvate in the presence of suitable enzymes. Since the enzymes required for the conversion of CMP or CDP into CTP are already contained in the crude microbial extracts used in accordance with the invention, the addition of exogenous enzymes is not necessary (in the processes described in the literature, e.g. Thiem et al., Augé et al., Simon et al. (1988, 1989, loc. cit) in some cases CTP is also produced in situ, but commercially available enzymes are employed).

Cell extracts of naturally occurring microorganisms having CMP-Neu5Ac synthetase activity that can be used in accordance with the invention are especially those of *Escherichia coli* serotype K1, species of Streptococcus serotype B or C, *Neisseria meningitidis, Pasteurella haemolytica, Pasteurella multacida, Moraxella nonliquefaciens, Citrobacter freundii,* Salmonella species, e.g. *S. dahlem, S. djakarta* or *S. trouca, Actinomyces viscosus,* and also *Corynebacterium parvum (Propionibacterium acnes).* In principle, cell extracts of any microorganism having CMP-Neu5Ac synthetase activity can be used. Cell extracts of *E. coli* strains of the serotype K1, especially *E. coli* K-235 (ATCC 13027), are preferred.

Such naturally occurring microorganisms having CMP-Neu5Ac synthetase activity can be converted in a manner known per se by mutation, for example using generally known mutagens, such as UV-rays or X-rays, or mutagenic chemicals, into mutants that are differentiated from their parents by improved properties, e.g. lower nutrient medium demands, higher growth rates and, especially, higher CMP-Neu5Ac synthetase activity. Such mutants can also occur spontaneously. The identification and isolation of such mutants is carried out also in a manner known per se: the CMP-Neu5Ac-synthetase activity of colonies of such mutants is ascertained, for example, after disintegration of the cells, by adding specific amounts of CTP and Neu5Ac to aliquot portions of the cell residue and qualitatively or quantitatively determining the CMP-Neu5Ac that has formed by means of chromatography, especially HPLC. Especially preferred mutants are those of *E. coli* K-235 with increased CMP-Neu5Ac synthetase activity and/or reduced slime formation. Such a spontaneously occurring mutant, called *E. coli* K-235/CS1, was isolated as a satellite colony of slimey *E. coli* K-235 colonies growing over a large area. The new mutant differs from the parent microorganism K-235 as follows: 1) colony morphology, 2) higher growth rate during fermentation and 3) higher specific activity in the shake culture and during fermentation, whilst the cell morphology (image under a microscope) and the spectrum of usable carbon sources are identical. The new strain *E. coli* K-235/CS1 also forms part of the present invention.

The reaction of the sialic acids, e.g. Neu5Ac, with CTP in the presence of the microbial cell extract is preferably carried out in homogeneous aqueous solution in the presence of approximately from 10–50, especially approximately from 20–40 mM $Mg^{2+}$, e.g. in the form of a corresponding halide or sulfate, e.g. $MgCl_2$ or $MgSO_4$, or in the presence of approximately from 5–30, especially approximately from 10–15 mM $Mn^{2+}$, e.g. in the form of a corresponding halide or sulfate, such as $MnCl_2$ or $MnSO_4$. The pH value of the reaction mixture is, in the presence of Mg-ions, adjusted to approximately 8–11, preferably 8–10, and, in the presence of Mn-ions, to approximately 6–8, preferably 7.5, and, for the stabilisation of the pH value, the reaction is carried out in a manner known per se in buffered solution or using a pH-stat. The reaction temperature is approximately from 20°–35° C., preferably approximately from 25°–30° C. The reactants are used preferably in equimolar amounts.

In the case of in situ generation of CTP, the procedure is analogous to that described above except that instead of CTP an equimolar amount of CMP (or CDP) and ATP or phosphoenolpyruvate (PEP) is used, it being possible for ATP and PEP optionally also to be used in excess, e.g. in a two- to three-fold excess.

The in situ generation of Neu5Ac from N-acetylmannosamine (Man2Ac) and pyruvate is carried out in the presence of a Neu5Ac aldolase. Since the pH optimum of the aldolase lies in the neutral range, the reaction is carried out at pH 6–8, preferably pH 7–7.5, which is why the use of $Mn^{2+}$ salts in the subsequent activation of the resulting Neu5Ac is preferred. Similarly, in the case of the in situ generation of Neu5Ac from N-acetylglucosamine and pyruvate the reaction is also carried out in the neutral range, for example pH 6–8, preferably pH 7–7.5, since both the N-acetylglucosamine epimerase to be added, which catalyses the conversion of the N-acetylglucosamine into N-acetylmannosamine, and, as described above, the Neu5Ac aldolase, have optimum activity in the neutral range. Consequently, in the last-mentioned case, too, the reaction is preferably carried out in the presence of $Mn^{2+}$ salts, in order to provide optimum conditions for the subsequent activation of the resulting Neu5Ac.

The activation of sialic acids, e.g. Neu5Ac, by CTP with the aid of microbial enzymes in accordance with the present invention can also be carried out in the presence of a pyrophosphatase, which removes from the reaction equilibrium the by-product of the reaction (the pyrophosphate), produced in addition to the desired main product (CMP-activated sialic acid), by means of hydrolysis into two equivalents of phosphate. In this manner the equilibrium position of the reaction can be shifted further towards the product, which is of advantage especially when using coupled enzyme systems consisting of Neu5Ac aldolase and CMP-Neu5Ac synthetase, or of N-acetylglucosamine epimerase and the above-mentioned aldolase and synthetase.

The process according to the invention can be carded out either as a batch process or continuously in an enzyme membrane reactor (EMR). In the latter case, the enzyme membrane reactor is preferably fitted with an ultrafiltration membrane having a separation limit of less than approximately 30000, so that the enzymes contained in the reaction mixture are held back whilst the low-molecular-weight product (CMP-activated sialic acid, e.g. CMP-Neu5Ac) and unreacted reactants pass through the membrane and the product can be isolated from the outflow. The reactor is preferably sterilised before use so that the addition of antibacterial substances can be dispensed with. The reactions are carried out in a manner analogous to that described above and, for the reasons given, if, for example, Neu-5Ac is used as starting material, either $Mn^{2+}$ or $Mg^{2+}$ salts may be used with simultaneous consideration of the optimum pH value, whereas in the case of the in situ preparation of Neu5Ac from N-acetylmannosamine or N-acetylglucosamine at a corresponding pH value the use of $Mn^{2+}$ salts is preferred. In the case of continuous production of CMP-activated sialic acids in an EMR it is advantageous for a pH monitor to be installed at the outlet (pH-probe) and for a pH regulator (pH-stat) to be installed at the inlet (addition of NaOH), which neutralises the pyrophosphate produced. In other respects, the parameters for the reaction in the enzyme membrane reactor are determined and selected as described for the preparation of Neu5Ac in an EMR according to German Offenlegungsschrift No. 3 937 891.

The process according to the invention can also be carded out by percolating the solution containing the reactants CTP and sialic acid, which has been adjusted to a suitable pH value, through a solid carrier on which the CMP-Neu5Ac synthetase contained in the crude microbial extract has been immobilised (the matrix-bound enzyme preparation is obtainable, for example, by percolation of the crude microbial extract through CNBr-activated Sepharose, eupergite or the like).

Working up the reaction mixture and purification of the CMP-activated sialic acids prepared in accordance with the invention are carried out by customary processes known from the State of the An. For example, the reaction mixture can be clarified by filtration or, preferably, centrifugation, and then the enzyme can be separated by ultrafiltration (membrane with separation limit of $\leq 30000$ Daltons) and the remaining product can be washed out of the retentate by diafiltration. The actual purification is then carried out, for example, by chromatographic methods, e.g. gel chromatography (inter alia Sephadex G-25), ion exchange chromatography, e.g. anion exchange chromatography, thin layer chromatography, HPLC or the like. The purification process can be simplified considerably if the cytidine nucleotides (CMP, CDP and CTP) still remaining in the reaction mixture when the reaction is complete are dephosphorylated using alkaline phosphatase.

In order to obtain the cell extract used in accordance with the process, a naturally occurring microorganism having cytidine 5'-monophospho-N-acetylneuraminic acid synthetase activity, especially one of those mentioned above, is cultivated in an aqueous nutrient medium that contains assimilable carbon and nitrogen sources and also mineral salts, at a pH value of approximately from 6 to 9, preferably of approximately from 6.5 to 7, and at a temperature of approximately 33°–40° C., especially approximately 37° C., the biomass is removed and the cell extract is obtained. The cultivation of the mentioned microorganisms is carded out aerobically (e.g. in shaken flasks), except in the case of *Corynebacterium parvum*, which is capable of multiplying only anaerobically or at very low oxygen partial pressures, e.g. by incubation in a thick layer with the exclusion of air and without stirring. The fermentation time is so selected that optimum titres with respect to CMP-Neu5Ac synthetase activity are achieved.

For the successful cultivation of suitable microorganisms good aeration (except in the case of *C. parvum*, see above), and also stepwise addition of the nutrients ("fed batch") are important. Suitable carbon sources are especially simple organic acids, such as acetic acid, malic acid, lactic acid or succinic acid, and also sugars, such as, especially, glucose or sorbitol. Suitable nitrogen sources are corresponding mineral salts, such as ammonium salts of inorganic acids, e.g. ammonium chloride or sulfate (e.g. in the case of *E. coli* and Salmonella species), and also complex nitrogen-containing mixtures, such as meat extract, yeast extract, casein hydrolysate, cornsteep liquor, Brain Heart Infusion, Trypticase Soy Broth etc., individually or in combination. The nutrient medium also contains a source of growth-promoting substances, such as vitamins, purines, pyrimidines, amino acids and trace elements, preferably in complex form (contained, for example, in the above-mentioned complex nitrogen-containing mixtures). In the case of some microorganisms that can be used in accordance with the invention, e.g. *E. coli*, it is also possible for mineral salt media having an organic carbon source, for example one of those mentioned above, to be used (optionally with the addition of defined growth-promoting substances). For good growth, some pathogenic microorganisms, such as Moraxella spec. and Pasteurella spec., require, in addition, the presence of haemin or other factors, which can be offered in the form of blood. It is advantageous to ascertain by experiment, in a manner known per se, the optimum cultivation parameters for the particular microorganism used.

When the cell density has reached an adequate value, the cultivation is discontinued. The culture broth is separated off in known manner, e.g. by centrifugation, and the sedimented cells are broken down in customary manner, e.g. by shaking with fine glass beads, by ultrasound treatment or using a French press. Insoluble cell components and, if used, glass beads, are removed, e.g. by centrifugation, and the residue is used as the enzyme source (crude extract). The residue, as a CMP-Neu5Ac synthetase-containing crude extract, can be used directly in the process according to the invention. Advantageously, however, in order to remove nucleic acids (viscous solutions!) the crude extract is treated with a polycationic agent, e.g. polyethyleneimine, a polyamine such as spermidine, streptomycinsulfate, or ribonuclease or $Mn^{2+}$ salts, and the precipitated nucleic acids are removed by centrifugation.

The separation of the cell debris from the cell homogenate can also be carried out by means of aqueous two-phase systems. For that purpose salts, such as sodium or potassium citrate, or sodium or potassium phosphate, and the disintegrated cell homogenate of *Escherichia coli* K-235 are added to polymers, such as polyethylene glycol (PEG) having molecular weights (MW) of from 400 to 20000, or dextran, but especially PEG having a MW of from 400 to 4000. The three components are mixed and/or shaken in the amounts given below. After centrifugation two phases result: an upper PEG-enriched phase, in which the major portion of the enzyme is found, and a lower salt-rich phase, in which cell debris, nucleic acids, accompanying protein and other solid components are concentrated. The preferred two-phase systems for use in accordance with the invention are composed as follows:

PEG (MW 1550 to 4000)in amounts of 16 to 20 w/v;
salts such as sodium citrate or potassium phosphate in amounts of 9–12 w/v;
pH value for the extraction approx. 7.0 to 8.5;
extraction temperature approx. 10°–20° C.

if desired a re-extraction can be carried out with a second phase system (not necessary if using *E. coli* K-235 as cell homogenate). This serves for the recovery of the synthetase from the PEG phase of the first phase system into the salt phase.

The removal of the synthetase from the other cell components by means of aqueous two-phase systems results in the simultaneous removal of the phosphatases and CTP-ases and nucleotidases, which in previous synthetase-purification methods have occasionally caused noticeable interference. The phosphatase activity can be checked by means of a test. For this test the substrate p-nitrophenyl phosphate (PNPP) is added to the enzyme sample, which is then incubated at 30° C. If phosphatases are present, they cleave the phosphate group of the nitro compound so that the yellow p-nitrobenzene results. The increase in the yellow colouring is monitored photometrically at 405 nm and is proportional to the amount of phosphatases present in the sample.

Preferably, the crude cell extract is subjected to one purification step in order to remove interfering components from the extract, such as e.g. CTP- and CMP-Neu5Ac-hydrolysing enzymes (if not using the aqueous two-phase system, see above) and neuraminic acid aldolases. It has been discovered, surprisingly, that a conventional purification step is adequate to obtain a cell extract that is excellently suitable for the process according to the invention.

For example a CMP-Neu5Ac synthetase preparation suitable for the reaction of sialic acids, e.g. Neu5Ac, with CTP can be obtained by precipitating that preparation with polyethylene glycol (PEG), PEG preferably having a molecular weight of approximately 200–20000, especially 400–6000, and being used in a concentration of approximately 10–50% (w/v), especially 15–40% (w/v). Alternative purification steps in the batch process are, for example, anion exchange chromatography (batchwise adsorption in the case of low salt concentration and desorption in the case of high salt concentration, e.g. 200–300 mM NaCl), e.g. on DEAE-Sephacel, DEAE-Sepharose, Q-Sepharose, QAE-Sephadex, Mono-Q and DEAE-Biogel, and hydrophobic interaction chromatography (HIC, adsorption in a batch process in the case of high salt concentration, e.g. 30% ammonium sulfate, desorption in the case of low salt concentration), e.g. on phenyl, octyl or butyl Sepharose, also butyl, hexyl or octyl agarose, alkyl Superose and butyl Fractogel etc. In particular, crude extracts purified by batch adsorption on anion exchangers or on hydrophobic gels can also be used for the in situ generation of CTP during the preparation of CMP-activated sialic acids according to the invention, ATP or phosphoenolpyruvate being used as phosphate group donor for the double phosphorylation of CMP to CTP. Further separating media suitable for the one-step purification of the crude cell extract are, e.g., hydroxy apatite, gel filtration, e.g. on Sephacryl, Superdex or Bio-Gel, metal chelate affinity chromatography, e.g. on chelating Sepharose or chelating Superose, and chromatofocussing.

The following combination is an especially preferred method of CMP-Neu5Ac synthetase purification:
removal of the cell debris from the cell homogenate by means of aqueous two-phase systems and purification by means of HIC.

This synthetase purification combination is simple to carry out. The aqueous two-phase systems and the HIC also make possible a problem-free increase in scale whilst still maintaining quality. The method produces good enzyme yields. The purified low-phosphatase enzyme can be used directly in the enzyme membrane reactor (EMR).

The crude cell extract having CMP-Neu5Ac synthetase activity, which has optionally been subjected to one purification step, can, if desired, be subjected to a concentration step for the purpose of reducing the volume of the solution. Such concentration steps include, for example, ultrafiltration, and also lyophilisation and protein precipitation with ammonium sulfate with subsequent uptake in a suitable buffer.

The starting materials used in accordance with the invention, such as CMP, CTP, sialic acids and the optionally used enzymes (Neu5Ac aldolase and N-acetylglucosamine epimerase) are commercially available or can be prepared in a manner known per se according to processes described in the literature.

The CMP-activated sialic acids obtainable in accordance with the present invention can be used in a manner known per se as building blocks for glycoconjugates (e.g. glycoproteins or glycolipids). Such glycoconjugates are of importance especially in the pharmaceutical and agrochemical fields, as well as generally for so-called "drug targeting". In this case CMP-activated sialic acid, e.g. Neu5Ac, acts as a substrate for sialyl transferases, which can transfer the saccharic acid to suitable acceptors, such as, e.g. to invertase treated with endoglucosidase H and enzymatically galactosylated, to enzymatically galactosylated rec.-tPA, to ovalbumin or to chemically modified bovine serum albumin (BSA). Thus the terminal galactose-Neu5Ac grouping serves, for example, as a mimic of the N-glycan chains of the complex type of human glycoconjugates. The correspondingly sialylated derivatives of rec.-tPA and of BSA have a prolonged half-life in blood plasma compared with the corresponding starting proteins (e.g. the proteins obtainable from transformed yeast by means of recombinant processes). Certain CMP-activated sialic acids, e.g. CMP-Neu5Ac, also have a pharmacological activity. For example CMP-Neu5Ac assists the regeneration of nerve cells.

The following Examples serve to illustrate the invention and are not intended to limit the invention in any way.

EXAMPLE 1

Optimisation of the Nutrient Solution a) Variation of the carbon source

The nutrient solution of the following composition, which was developed by Uchida et al. (*Agr. Biol. Chem.* (1973) 37, 2105–2110) for obtaining "Colominic Acid" using *Escherichia coli*, is used as a basis for the optimisation of the nutrient medium for the production of CMP-Neu5Ac synthetase from *Escherichia coli* K-235 (ATCC 13027):

| | |
|---|---|
| sorbitol | 20 g/l |
| yeast extract | 0.5 g/l |
| $K_2HPO_4$ | 14 g/l |
| $(NH_4)_2SO_4$ | 5 g/l |
| $MgSO_4 \times 7H_2O$ | 0.5 g/l |
| pH value | 7.8 |

3 carbon sources, each of 10 g/l, are added to this nutrient solution without sorbitol in 10 different batches. In addition, 100 ml Erlenmeyer flasks each containing 20 ml of the corresponding medium are sterilised by autoclaving for 20 minutes at 121° C., and inoculated with cells of Escherichia coli K-235, cultivated on a suitable solid culture medium. The cultures are cultivated aerobically at 37° C. and 220 revs/min in a shaker. After 15-16 h the contents of the shaken flasks are centrifuged (20 min., 8000× g in a cooled centrifuge) and the sedimented cells are suspended in a buffer solution of pH 9, consisting of 50 mM tris/HCl, 1 mM dithiothreitol and 20 mM $MgCl_2$.

The microorganisms in that suspension are broken down by shaking with fine glass beads. In an Eppendoff reaction vessel, 1.2 g of glass beads (0.1–0.3 mm diameter) are added to 0.6 ml of suspension and then, by means of special inserts, shaken for 10 min. at maximum speed in a vibratory mill manufactured by Retsch (Haan, FRG). Insoluble cell components and glass beads are removed by centrifugation (13000 revs/min, Biofuge A, Messrs Hereus, Osterode, FRG) and the residue is used as the enzyme source (crude extract).

The batches for the activity determination contain:

| | |
|---|---|
| 1.5M tris/HCl buffer, pH 9 | 25 μl |
| 0.4M $MgCl_2$ | 25 μl |
| 0.01M dithiothreitol | 25 μl |
| 0.1M Neu5Ac | 25 μl |
| deionised water | 100 μl |
| enzyme solution | 25 μl |

The enzyme reaction is initiated by the addition of 25 μl of a 0.1 M CTP-solution. For the qualitative analysis, after approximately 175 min. incubation at 30° C. a 4 μl sample is taken from each batch and separated by thin layer chromatography on silica gel plates (type 60 F-254, Merck, Darmstadt, FRG). The mobile phase used is a mixture of ethanol, 95%, and ammonium acetate, 1M, in a ratio of 7:3. The detection is carried out in UV light at 254 nm. After 3 hours' incubation, the enzyme reaction is stopped by the addition of 250 μl of cold acetone. The batches are cooled in an ice-bath for 10 min., and then the precipitates of protein and salts are removed by centrifuging for 10 min. at 13000 revs/min in a Biofuge A.

The quantitative determination of the reaction product CMP-Neu5Ac is carried out by means of HPLC using an amino-nucleosil column as stationary phase (250×4 mm, 10 μm particle diameter, Innovativ Bischoff AG, Wallisellen). The injection volume is 7 μl. Elution is carried out for 8 minutes on a gradient in which the potassium phosphate concentration (pH 7) increases from 3 to 250 mM and the acetonitrile concentration decreases from 50 to 0%. The calculation of the CMP-Neu5Ac concentration is carried out by way of an external standard (0.25 mM, CMP-Neu5Ac, sodium salt; Sigma, Buchs, Switzerland) by way of integration of the area under the peaks.

The enzyme activity is given in International Units, one unit (U) corresponding to an amount of 1 μmol of CMP-Neu5Ac foraged per minute. With a specific activity of 1 μmU/mg a conversion rate of 1 nmol per minute per mg of protein (Biorad-Proteintest, Biorad-Laboratories, Glattbrugg) is indicated.

As Table 1 shows, the E. coli strain used has the highest synthetase activity when grown on sorbitol and that sugar alcohol is therefore used as carbon source for the production of the enzyme.

TABLE 1

Variation of the carbon source for the production of CMP-Neu5Ac synthetase from Escherichia coli K-235

| C source (10 g/l) | growth | spec. activity (mU/mg) | yield/volume (U/l) |
|---|---|---|---|
| sorbitol | +++ | 8.27 | 1.22 |
| succinate | + | 1.71 | 0.04 |
| malate | + | 2.04 | 0.06 | b) Variation of the nitrogen source

Various complex laboratory nutrients and commercial nutrients, each in an amount of 5 g/l, are used as nitrogen source in the "Colominic Acid" production medium without yeast extract (see Example 1a). In addition, that medium with 5 g/l yeast extract and without ammonium sulfate is supplemented by 8 pure nitrogen-containing substances which are used in molar concentrations with respect to the nitrogen content that correspond to 5 g/l of ammonium sulfate. The procedure is otherwise as in Example 1a.

As Table 2 shows, a high enzyme production can be achieved with various complex and synthetic nitrogen sources, such as e.g. yeast extract, peptone or cornsteep liquor and ammonium sulfate, glummate and asparagine. In the following, yeast extract of commercial quality on account of the high specific activity, and ammonium sulfate on account of the high yield/volume, are used for the production of the synthetase.

TABLE 2

Variation of the nitrogen source in "Colominic Acid" production medium

| N source | growth ($OD^{660}$) | spec. activity (mU/mg) | yield/volume (5 g/l) (U/l) |
|---|---|---|---|
| a) Test 1: Laboratory and commercial nutrients, 24 h cultivation ||||
| yeast extract (Fluka) | +++ | 12.9 | 1.84 |
| meat extract | +++ | n.d. | 1.69 |
| Lab Lemco powder | ++ | 5.14 | 0.89 |
| peptone, trypt. digested | +++ | 11.1 | 1.67 |
| fish peptone FPH-30 | +++ | 2.76 | 0.37 |
| fish peptone H-0100 | +++ | 10.0 | 1.56 |
| b) Test 2: complex commercial nutrients, 16 h cultivation ||||
| without | 0.55 | 0.0 | 0.0 |
| yeast extract (Fluka) | 3.90 | 12.21 | 4.51 |
| yeast extract, comm. | 6.28 | 15.4 | 4.77 |
| casamino acids | 4.13 | 14.0 | 4.77 |
| casein hyrolysate | 5.30 | 11.5 | 4.03 |
| cornsteep liquor | 7.15 | 14.9 | 4.77 |
| peanut flour | 5.7 | 10.6 | 3.17 |
| fish peptone H-0230 | 5.45 | 8.22 | 3.30 |
| fish peptone H-0430 | 5.88 | 12.3 | 4.77 |
| fish peptone P-100 | 5.33 | 12.3 | 5.13 |
| whey powder, sweet | 2.05 | 7.22 | 1.10 |
| peptone C | 6.35 | 14.9 | 4.77 |
| soybean flour, full fat | n.d. | 2.62 | 1.10 |
| soybean flour fat removed | 5.95 | 8.423 | 2.57 |
| c) Test 3: synthetic N sources, 16 h cultivation: ||||
| $(NH_4)_2SO_4$ | n.d. | 16.8 | 6.20 |
| $NH_4Cl$ | n.d. | 14.0 | 3.79 |
| $NH_4$-acetate | n.d. | 12.4 | 5.17 |
| L-aspartate | n.d. | 10.0 | 3.10 |
| L-asparagine | n.d. | 19.5 | 5.79 |
| L-glutamate | n.d. | 15.3 | 4.76 |
| L-lysine | n.d. | 11.0 | 2.66 |
| L-proline | n.d. | 17.8 | 4.83 | n.d.: not determined c) Variation of the sorbitol concentration

In shake cultures using "Colominic Acid" production medium with 5 g/l yeast extract, the sorbitol concentration is varied in the following steps: 0, 0.5, 1.25, 2.5, 5, 7.5, 10.0 and 20.0 g/l. The test is carried out as described in Example 5a.

With sorbitol concentrations greater than 2.5 g/l the enzyme production is good, production being optimum at 5–10 g/l.

d) Variation of the yeast extract concentration

Shake culture tests according to Example 1a) with "Colominic Acid" production medium containing 10 g/l of sorbitol are initiated with the following yeast extract concentrations: 0, 0.5, 1.0, 2.5, 5.0, 7.5 and 10.0 g/l.

Between 1 and 10 g/l of yeast extract a high enzyme content is measured in the crude extract, the highest values being obtained at 1 and 2.5 g/l.

e) Variation of the starting pH value

Growth and CMP-Neu5Ac synthetase production are examined in the manner described in a) in shake cultures using "Colominic Acid" production medium, with the starting pH value ranging from 5.5 up to 10 units in units of 0.5.

More than 50% of the maximum yield/volume (U/l of fermentation broth) is obtained between a starting pH of 5.5 and 8.5. The optima for the yield/volume (6.0 U/l) and the specific activity (20 mU/mg) lie at pH 6.5.

EXAMPLE 2

Fermentative Production of the Biomass a) Fermentation with subsequent addition of sorbitol and yeast extract To cultivate the precultures two 500 ml Erlenmeyer flasks each containing 100 ml of the nutrient solution of the following composition, optimised in accordance with Example 1, are sterilised by autoclaving for 20 min. at 120° C. and inoculated with cells of *Escherichia coli* K-235 (ATCC 13027), cultivated on a suitable solid nutrient medium.

The nutrient solution has the following composition:

| | |
|---|---|
| sorbitol | 10 g/l |
| yeast extract | 2.5 g/l |
| $K_2HPO_4$ | 11 g/l |
| $(NH_4)_2SO_4$ | 2.5 g/l |
| $MgSO_4 \times 7H_2O$ | 1 g/l |
| pH value | 6.5 |

The cultures are shaken for 15–16 h at 37° C. and 220 revs/min.

10 l of the above-mentioned medium, but with 6 g/l of sorbitol, are sterilised in a bio-reactor of 15 l total volume by heating at 121° C. for 30 min. Foam control and regulation of the concentration of dissolved oxygen and of the pH value are carried out automatically by means of the control unit of the system. The pH value is regulated by the addition of 5N $H_3PO_4$ and 5N NaOH and the concentration of dissolved oxygen is regulated by the number of revolutions of the stirrer. The operating parameters are:

| | |
|---|---|
| temperature | 37° C. |
| pH value | 6.5 |
| dissolved oxygen concentration | 50% saturation |
| maximum number of revolutions of the stirrer | 1200 revs/min |
| maximum aeration rate | 20 Nl/min = 2.0 vvm |

(vvm: volume (air)/volume (fermenter content)/min.)

The bioreactor is inoculated with 150 ml of preculture and, in samples of culture broth removed under sterile conditions, every 30 min. the biomass is monitored by measuring the optical density at 660 nm and the enzyme content is monitored by determining the CMP-Neu5Ac synthetase activity in the crude extract over time (see Example 1). At an optical density of 3.8, 10.5 and 16.8,400 ml of a sterile solution with 150 g/l of sorbitol and 62.5 g/l of yeast extract are added under aseptic conditions. After reaching the maximum cell density the biomass is removed by sedimentation in a continuous flow centrifuge and stored frozen at −20° C.

The maximum OD obtained at 660 nm is 20.8, corresponding to a moist mass content of 45 g/l, and the maximum enzyme yield is 28 U/l of fermentation medium, at a specific activity of 17 mU/mg of protein in the crude extract without nucleic acid precipitation (see Example 3).

b) Fermentation with subsequent addition of sorbitol, yeast extract, $MgSO_4$ and ammonia Compared with Example 2a), the following changes are made:

$MgSO_4$ is autoclaved as a 100-fold concentrated solution separately from the other medium components, 30 mg/l of $CaCl_2$ are added to the medium, the pH regulation is carried out with 12.5 % ammonia solution instead of 5N NaOH, in the course of the fermentation, yeast extract and sorbitol are subsequently fed in 10 times in the above-mentioned amounts, at a cell density of $OD^{660}=50$, 70 ml of a sterile $MgSO_4$ solution (100 g/l) are added.

A maximum $OD^{660}$ of 70.3, a bacterial moist mass content of 195 g/l and an enzyme yield/volume of 67 U/l of fermentation broth are achieved.

EXAMPLE 3

Production of the Crude Extract 200 g of bacterial mass (obtained according to Example 2) are resuspended with 300 ml of a buffer solution of pH 9, consisting of 50 mM tris/HCl, with 1 mM dithiothreitol and 20 mM $MgCl_2$. The cells are disintegrated in an ultrasound apparatus with cooling in an ice-bath until over a period of time no further increase of the protein concentration in the solution is registered. 20.8 ml of a 10% solution of polyethylene irainc having a mean molecular weight of $6 \times 10^5$ to $1 \times 10^6$, pH 9, are added to the cell homogenate and the whole is incubated in an ice-bath for 15 min. with occasional stirring, and then the precipitated nucleic acids and a major portion of the cell debris is removed by sedimentation for 60 min. at 23000× g and 4° C. in a cooled centrifuge. For further removal of suspended matter the crude extract is subjected to a second centrifugation step for 30 min. at 40000× g and 4° C. The product solution (370 ml total volume) has an activity/volume of 0.18 U/ml and a specific activity of 9 mU/mg of protein. By comparison with Example 2 it is evident that the breakdown of cells using glass beads renders possible higher synthetase yields than disintegration by ultrasound. As demonstrated by the reaction rates determined before and after the polyethylene irainc precipitation, the nucleic acids can be separated by this step without loss of CMP-Neu5Ac synthetase activity.

EXAMPLE 4

Fermentative Production of CMP-Neu5Ac Synthetase-Containing Crude Extract of *E. coli* K-235 on a 200 l Scale Apart from the changes below, the procedure is as in Example 2b and, unless specified to the contrary, there is a general increase in scale by a factor of 20:

130 l of medium are sterilised in a 300 l fermenter and inoculated with 1000 ml of preculture, The aeration rate is adjusted manually as required during fermentation (0.5–1 vvm). The fine control of the concentration of dissolved oxygen is carried out by automatic variation of the number of revolutions.

After reaching an $OD^{660}$ of 4.3, 70 l of a previously autoclaver concentrated sorbitol/yeast extract solution (159 g/l of sorbitol and 66 g/l of yeast extract) are continuously added under sterile conditions over a period of 14 h. During this the pump speed is adjusted manually such that the number of revolutions of the stirrer and thus the oxygen consumption are exactly maximum.

After 26 h the maximum cell density is achieved, the $OD^{660}$ being 40.3. The fermenter contents are cooled to 4° C. by means of a brine-containing cooling agent, and the cells are sedimented in a throughflow centrifuge and disintegrated by being passed twice through a high-pressure homogenizer. After the disintegration of the cells the enzyme yield in the crude extract is 8300 U with a specific activity of 12.2 mU/mg.

EXAMPLE 5

Production of enzyme preparations having increased CMP-Neu5Ac synthetase activity a) Precipitation of CMP-Neu5Ac synthetase with polyethylene glycol 185 ml of a 50% solution (w/w, density=1.08 kg/l) of polyethylene glycol having a molecular weight of 6000 are added to 370 ml of crude extract (see Example 3) and the batch is incubated overnight in an ice-bath. The precipitated protein is sedimented by centrifugation at 4° C. and 40000× g for 1 h and the pellet is dissolved in 100 ml of enzyme buffer (=50 mM tris/HCl, 1 mM dithiothreitol, pH 7.5). The enzyme preparation obtained in that manner has a specific activity of 40 mU/mg and an activity/volume of 0.52 U/ml and is substantially free of CTPase.

b) Production of a CMP-Neu5Ac synthetase preparation by batch adsorption on butyl-Fractogel TSK 450 ml of ice-cooled crude extract are mixed with 194 ml of saturated ammonium sulfate solution (=100%) and 600 ml of butyl-Fractogel TSK (Merck, Darmstadt, FRG), which has previously been washed over a G3 sintered glass frit with 1.8 l of a 30% ammonium sulfate solution in enzyme buffer (see Example 5a)). After 15 min. incubation at 4° C. with gentle stirring, the gel is suction-filtered over a glass frit and washed with 1.2 l of a 30% and with 1.8 l of a 15% ammonium sulfate solution in ice-cooled enzyme buffer. Elution is carried out with 1.8 l of ice-cooled enzyme buffer without ammonium sulfate. The eluate is concentrated to 200 ml by ultrafiltration at 4° C. using a tangential flow system type DC-2 through an H1P30-43 hollow fibre membrane module with a separation limit of 30000 Daltons (both Grace, Division Amicon, Lausanne).

The concentration of CMP-Neu5Ac synthetase in the retentate is 0.12 U/ml with a specific activity of 11 mU/mg. The concentration by ultrafiltration proceeds without loss of enzyme activity. The enzyme preparation, to which 43.5% w/v of glycerol has been added, can be stored at −20° C. for months without loss of activity.

c) Production of a CMP-Neu5Ac synthetase preparation by batch adsorption on QAE-Sephadex 5 ml of QAE-Sephadex A50 gel are washed with 20 ml of ice-cooled potassium phosphate buffer, 50 mM, pH 7.5, in a filter tube with a porosity of 1 and incubated with 2.9 ml of crude extract (see Example 3) for 15 min. at 0° C. with gentle stirring to adsorb the protein. After suction-filtering off the protein solution, the gel is washed 5 times with 5 ml of the above-mentioned phosphate buffer each time. The desorption of the protein is carried out with sodium chloride solutions of increasing concentration (0.1, 0.13, 0.17, 0.2, 0.3 and 1M) in the said phosphate buffer. For this each time 12.5 ml of the corresponding ice-cooled NaCl solution is mixed with the gel, incubated for 5 min. at 4° C., and then suction-filtered, and 3 ml of the eluate are desalted over a 10 ml gel filtration column (Econ-Pac 10DG, Biorad, Glattbrugg). The determination of the protein concentration and of the enzyme content shows that in the case of 0.2–0.3M NaCl the synthetase is desorbed from QAE-Sephadex with a 33% yield and a mean specific activity of 21 mU/mg.

d) Production of a CMP-Neu5Ac synthetase preparation by batch adsorption on hydroxy apatite 2 ml of a crude extract obtained according to Example 3 are incubated for 15 min. at 4° C., with occasional stirring, with 10 ml of hydroxy apatite (Biorad-Laboratories, Glattbrugg), which has previously been washed on a glass frit with 30 ml of enzyme buffer. After suction-filtering off the sample solution, the gel is rinsed with 30 ml of a 100 mmolar solution of potassium phosphate, pH value 7.5. The desorption is carried out with 2×15 ml of ice-cooled 0.2 molar and 1×15 ml of 0.4 molar potassium phosphate buffer of pH 7.5. For that purpose in each case the corresponding buffer solution is added to the suction-filtered gel and, after 10 min. incubation at 4° C., the whole is again suction-filtered over a glass frit. The combined eluates are concentrated to 2 ml with an ultrafiltration cell type CEC1 through a YM 30 membrane with a separation limit of 30000 Daltons (both Grace, Division Amicon, Lausanne).

The determination of the activity and of the protein in the retentate, which has been desalted over an Econ-Pac 10DG gel filtration column (final volume 4 ml), shows an activity/volume of 0.062 U/ml and a specific activity of 26 mU/mg.

EXAMPLE 6

Synthesis of CMP-Neu5Ac using Enzyme Preparations of *Escherichia coli* K-235 obtained in accordance with Example 5 a) Variation of the CTP and Neu5Ac concentrations

The CTP and Neu5Ac concentrations (see Table 3) are varied in batches of the following composition:

| | |
|---|---|
| tris/HCl buffer, pH 9 | 0.15M |
| dithiothreitol | 1.0 mM |
| CTP and Neu5Ac, each (both Fluka, Buchs) | 5–50 mM |
| $MgCl_2$ | 40–65 mM |
| CMP-Neu5Ac synthetase | 20–200 mU/ml |

Since, in the course of the reaction, $Mg^{2+}$ is precipitated with pyrophosphate in the form of magnesium pyrophosphate, in the case of reactant concentrations of 30 and 50 mM the $MgCl_2$ is used at 15 mM in excess with respect to the reactants. The source of the CMP-Neu5Ac synthetase is an enzyme preparation prepared in accordance with Example 5a) by precipitation with polyethylene glycol, having 0.71 U/ml activity/volume and 34 mU/mg specific activity. 4.7 U of synthetase are used to convert 1 mmol of reactant.

After 24 h incubation at 30° C. the batches are worked up as described in Example 1. Before injection onto the HPLC column, the samples are diluted to a reactant starting concentration of 2 mM.

As Table 3 shows, the highest CMP-Neu5Ac concentration is achieved at a concentration of the reactants of 20 mM each. The molar yields decrease as the reactant concentration increases. By measuring the product concentration during the course of the reaction it is possible to ascertain the maximum yield and to stop the reaction at the correct point in time.

TABLE 3

Synthesis of CMP-Neu5Ac as a function of the concentration of the reactants CTP and Neu5Ac

| CTP/Neu5Ac (mM) | Enzyme conc. (mU/ml) | $MgCl_2$ (mM) | CMP-Neu5AC (mM) | molar yield (%) |
| --- | --- | --- | --- | --- |
| 5 | 24 | 40 | 4.8 | 96 |
| 10 | 47 | 40 | 9.1 | 91 |
| 15 | 71 | 40 | 12.9 | 86 |
| 20 | 94 | 40 | 16.3 | 81 |
| 30 | 141 | 45 | 13.6 | 45 |
| 50 | 235 | 65 | 0.8 | 1.6 | b) In situ generation of CTP from CMP and ATP

The synthesis of CMP-Neu5Ac with the generation of CTP from ATP and CMP is investigated using 2 enzyme preparations that have been obtained in accordance with Example 5 (see Table 4). Each of the reactants is used in a concentration of 10 mM and otherwise the procedure is as in Example 6a). In parallel, control batches are prepared with CTP and Neu5Ac.

As can be seen from Table 4, the preparation of CMP-Neu5Ac with the in situ generation of CTP from ATP and CMP using the enzyme solutions obtained according to Examples 5b) and 5c) is possible with approximately 50% of the yield achieved with CTP.

TABLE 4

Synthesis of CMP-Neu5Ac from ATP, CMP and Neu5Ac (each 10 mM)

| Enzyme prep./ Example | Enzyme conc. (mU/ml) | pH value | CMP-Neu5Ac from | |
| --- | --- | --- | --- | --- |
| | | | ATP + CMP (mM) | CTP (mM) |
| butyl-Fractogel/ 5b) | 28 | 7.5 | 3.03 | 5.66 |
| butyl-Fractogel/ 5b) | 28 | 9 | 3.17 | 6.27 |
| QAE-Sephadex 5c) | 20 | 9 | 3.98 | 7.83 | c) In situ generation of CTP from phosphoenol pyruvate and CMP

Synthesis batches are prepared with 25 mM phosphoenolpyruvate, 10 mM CMP and 10 mM Neu5Ac in accordance with the procedure described in Example 6a). The synthetase preparations used appear in Table 5.

The synthesis of CMP-Neu5Ac from phosphoenolpyruvate, CMP and Neu5Ac with more than 50% of the yield via CTP is possible both with the product of the batch adsorption on butyl-Fractogel and with crude extract.

TABLE 5

Synthesis of CMP-Neu5Ac from phosphoenolpyruvate, CMP and Neu5Ac (10 mM)

| Enzyme prep./ according to Example | Enzyme conc. (mU/ml) | pH value | CMP-Neu5Ac from | |
| --- | --- | --- | --- | --- |
| | | | PEP*) + CMP (mM) | CTP (mM) |
| crude extract/ 3) | 35 | 7.5 | 4.19 | 6.7 |
| crude extract/ 3) | 35 | 9 | 3.87 | 6.89 |
| butyl-Fractogel/ 5b) | 28 | 7.5 | 5.21 | 9.73 |
| butyl-Fractogel/ 5b) | 28 | 9 | 7.84 | 9.89 |

*): PEP: phosphoenolpyruvate d) In situ generation of Neu5Ac from Man2Ac and pyruvate The synthesis of CMP-Neu5Ac from Man2Ac, pyruvate and CTP by coupling a neuraminic acid aldolase with the CMP-Neu5Ac synthetase reaction is examined as a function of the concentration of reactant. Since the optimum pH of the aldolase lies in the neutral range, the reaction is carried out at pH 7.5 in the presence of $MnCl_2$ to activate the synthetase. The substrates Man2Ac and CTP are used in equimolar ratio, pyruvate in double the molar amount and 5 mM $MnCl_2$ in excess in relation to Man2Ac and CTP. The enzymes used are a Neu5Ac aldolase preparation (Toyobo, Japan) and an enzyme solution having synthetase activity that has been produced by precipitation with polyethylene glycol in accordance with Example 5a). The concentration of the aldolase (specific activity 8 U/mg) is 0.5 mg and that of the synthetase 4.7 U, each per 1 mmol of Man2Ac or CTP to be reacted. The test is carried out as described in Example 6a).

As Table 6 shows, the product concentration and the molar yield increase with the reactant concentration to a maximum of 18.4 mM or 37%.

TABLE 6

Synthesis of CMP-Neu5Ac from Man2Ac, pyruvate and CTP catalysed by Neu5Ac aldolase and CMP-Neu5Ac synthetase

| Man2Ac/CTP (mM) | pyruvate (mM) | $MgCl_2$ (mM) | CMP-Neu5AC (mM) | molar yield*) (%) |
| --- | --- | --- | --- | --- |
| 5 | 10 | 10 | 0.52 | 10 |
| 10 | 20 | 15 | 2.3 | 23 |
| 15 | 30 | 20 | 5.06 | 34 |
| 20 | 40 | 25 | 6.62 | 30 |
| 30 | 60 | 35 | 11.1 | 37 |
| 50 | 100 | 55 | 18.4 | 37 |

*)molar yields based on Man2Ac and CTP e) In situ generation of Neu5Ac from N-acetylglucosamine and pyruvate In the synthesis of CMP-Neu5Ac from N-acetylglucosamine, pyruvate and CTP, N-acetylglucosamine is epimerised to Man2Ac by means of an N-acetylglucosamine epimerase. Catalysed by the Neu5Ac aldolase used in Example 6d), Man2Ac condenses with pyruvate to form Neu5Ac.

The reaction batch with a total volume of 250 μl contains:

| | |
|---|---|
| tris/HCl-buffer | 150 mM |
| MnCl$_2$ | 55 mM |
| dithiothreitol | 1 mM |
| CTP | 50 mM |
| sodium pyruvate | 100 mM |
| N-acetylglucosamine | 200 mM |
| N-acetylglucosamine epimerase (Toyobo, Japan) | 300 mU/ml |
| Neu5Ac aldolase | 200 mU/ml |
| CMP-Neu5Ac synthetase | 235 mU/ml |
| pH value | 7.1 |

An enzyme preparation obtained by precipitation with polyethylene glycol (see Example 5a) is used as the synthetase source. The procedure is otherwise in accordance with Example 6a).

After 20 h incubation at 30° C., a CMP-Neu5Ac concentration of 5.3 mM corresponding to a conversion of approximately 10%, based on CTP, is determined by means of HPLC.

f) Preparative synthesis of CMP-Neu5Ac as a pure substance

A batch of the following composition is incubated for 20 h at 30° C. in a water bath with gentle stirring:

| | |
|---|---|
| tris/HCl, pH 9 | 150 mM |
| MgCl$_2$ | 40 mM |
| dithiothreitol | 1 mM |
| Neu5Ac | 15 mM |
| CTP | 15 mM |
| CMP-Neu5Ac synthetase preparation according to Example 5a) | 7.04% v/v (corresponding to 0.05 U/ml final conc.) |
| pH value | 9, adjusted with dilute NaOH |
| total volume | 150 ml |

All the steps for working up the CMP-Neu5Ac are carried out at from 0°–4° C. Precipitates are removed by centrifuging for 20 min. at 25000× g, are resuspended in 150 ml of a 10 mmolar NH$_3$ solution and are removed again by centrifugation. After repeating this washing step, the protein is separated from the combined residues by means of ultrafiltration through a YM 30 membrane (separation limit 30000 Daltons (Grace, Division Amicon, Lausanne) in a CEC1 throughflow concentrator produced by the same manufacturer. In the case of a retentate volume of 15 ml, this is diluted with 15 ml of NH$_3$ solution (1 mM) and concentrated to 15 ml again. This diafiltration step is repeated twice.

The filtrate (480 ml) is applied at a flow rate of 25 ml/h to a 5×25 cm Dowex 1×8 column (200–400 mesh, bicarbonate form ), which has previously been washed with 2 column volumes of 1 mM NH$_3$. The column is then washed with 1 l of NH$_3$ solution (1 mM). Elution is carried out at the above-mentioned flow rate on a linear gradient (2×5 l) of 0.01–1M triethylammonium hydrogen carbonate, pH 8.4. The CMP-Neu5Ac-containing fractions are identified by means of thin layer chromatography (see Example 1), combined and lyophilised.

The removal of contamination with CMP is carried out by means of gel chromatography on Sephadex G-25 (Pharmacia). For that purpose 0.29 g of the lyophilisate is dissolved in 16 ml of 1 mM NH$_3$ solution and the sample solution is conveyed at a flow rate of 70 ml/h through the column (5×80 cm), which has previously been equilibrated with 4.5 l of NH$_3$ solution (1 mM). To work up the total product of the anion exchange chromatography the gel filtration step is carried out 3 times. Those fractions that according to thin layer chromatography analysis contain only CMP-Neu5Ac are combined and freeze-dried. 0.79 g of the ammonium salt of CMP-Neu5Ac is obtained.

EXAMPLE 7

Removal of the Cell Debris by Means of Aqueous Two-Phase Systems

A pH of 7.50 and a T of 10° C. are established as optimum in preliminary tests. The cell homogenate is thawed by microwave, but a temperature of 10° C. must not be exceeded. The cell homogenate and the phase systems that have been removed by centrifugation are kept at all times in an ice bath.

The polymer PEG having a molecular weight of 1550 (PEG-550) in various final-concentrations of 16.87–17.61% w/w is mixed together with trisodium citrate×6 H$_2$O in final concentrations of 9.69–9.84% w/w and with cell homogenate (CH) from E. coli K-235 (47.65–46.04% w/w final concentration). The trisodium citrate×6 H$_2$O is used in the form of a 40% (w/v) solution, the pH value of which has previously been adjusted to 7.50 using a 40% (w/v) citric acid solution. The batches are made up to 100% total weight (=10–600 g) with deionized water and shaken for 5 min. manually or using a shaker. The phase systems are then removed by centrifuging for 20 min. at 8000 revs/-min in a cooled centrifuge at 4° C.

The following compositions prove optimum for the synthetase extraction:

Composition 1: 16.87% w/w PEG-1550+9.69% w/w trisodium citrate×6 H$_2$O+47.65% w/w CH, Composition 2: 17.61% w/w PEG-1550+9.84% w/w trisodium citrate×6 H$_2$O+46.04% w/w CH, 2.7 U of synthetase are extracted into the upper phase of a 10 g phase system of composition 1 (5.4 ml, 1.75 mg of protein/ml) in a yield of 96%, and 2.32 U, corresponding to a yield of 90%, are extracted into the upper phase of a 10 g system of composition 2 (5.3 ml, 1.71 mg of protein/ml).

The resulting two phases are separated, the PEG 1550-enriched upper phase being cleanly decanted off from the lower phase. The upper phase, which contains the CMP-Neu5Ac synthetase and PEG-1550, is used for further purification by means of hydrophobic interaction chromatography (HIC).

The following stock solutions are prepared to determine the phosphatase activity: the reagent=10 mM 4-nitrophenyl phosphate (PNPP, Serva) of pH 8.0, 7 mM MgCl$_2$ in 100 mM tris-HCl, pH 8.0, and 100 mM tris-HCl, pH 8.0.

To determine the phosphatase activity, 100 μl of PNPP, 10 μl of MgCl$_2$ and 880 μl of tris-HCl buffer are added to 10 μl of the sample to be examined. The extinction is measured at 401 nm immediately and also after 20 min. incubation at 30° C. The concentrations of freed 4-nitrophenol are determined by means of a standard solution of 4-nitrophenol. The following phosphatase activites are determined (1 U=1 μmol of formed 4-nitrophenol/min.):

| Sample | Phosphatase activity (U/ml) |
|---|---|
| cell homogenate | 0.347–0.353 |
| upper phase | 0.04–0.09 |
| lower phase | 0.142–0.162 |
| HIC fraction/throughflow (see Example 8) | 0.0013 |
| HIC fraction/synthetase (see Example 8) | 0.003 |

EXAMPLE 8

Hydrophobic Interaction Chromatography a) Purification of the synthetase by means of hydrophobic interaction chromatography (HIC) (A)

Sample: 3 ml of upper phase from Example 7 with the synthetase. Matrix: phenyl-Sepharose CL-4B, Pharmacia. Capacity: 15–20 mg HSA (human serum albumin)/ml gel. Column: 26 mm diameter×4 cm high-=approx. 50 ml gel bed. Flow rate: 1.53 ml/min. Eluant A: 50 mM $Na_2HPO_4$+1.8M $(NH_4)_2SO_4$, pH 7.0. Eluant B: 50 m $Na_2HPO_4$, pH 7.0. Gradient: 0–100% B in 2.5 h, linear gradient. Detection: UV, 280 nm.

After the column has been purified with at least three bed volumes of 3M urea solution, then rinsed with water and equilibrated with buffer A, 200 ml of the synthetase-containing upper phase are applied to the phenyl-Sepharose CL-4B column. The HIC column is then rinsed with buffer A until all non-bound protein has been rinsed off. Elution is then carried out with a linear gradient of 0% B to 100% B with 250 ml of A and 250 ml of B. In the course of this the ion strength is considerably reduced. After the gradient, rinsing is carried out with eluant B for 30 min and then with water, in order to desorb the synthetase from the column. The elution is followed by a Pharmacia UV monitor at 280 nm. 14 U of synthetase from 20 ml of the upper phase with a protein concentration of 13.58 mg/ml are purified with a 98.87% recovery rate.

b) Purification of the synthetase by HIC (B)

Sample: PEG-1550-containing upper phase with the synthetase. Matrix: phenyl-Sepharose CL-4B. Capacity: 15–20 mg of HSA per ml of gel. Column: 26 mm diameter×4 cm height=approx. 50 ml gel bed. Flow rate: 1.53 ml/min. Buffer A: 50 mM $Na_2HPO_4$+1.8M $(NH_4)_2SO_4$, pH 7.0. Buffer B: 50 mM $Na_2HPO_4$, pH 7.0. Gradient: 0–100% B in 2.5 h, stepped gradient. Detection: UV, 280 nm.

The conditions of Example 8a) are used in this test except that in this case elution is carried out with a stepped gradient. The yield in this case is approximately 85%.

c) Purification of the synthetase by HIC (C)

Sample: PEG-1550-containing upper phase with the synthetase. Matrix: phenyl-Sepharose CL-4B. Capacity: 15–20 mg of HSA per ml of gel. Column: 26 mm diameter×4 cm height=approx. 50 ml gel bed. Flow rate: 1.53 ml/min. Buffer A: 50 mM $Na_2HPO_4$+1.8M $(NH_4)_2SO_4$, pH 7.0. Buffer B: 50 mM $Na_2HPO_4$, pH 7.0. Eluant: 10% v/v ethylene glycol in water. Gradient: 0–100% B in 2.5 h, linear gradient. Detection: UV, 280 nm Procedure in this case is as in Example 8a. Here, the synthetase is desorbed from the hydrophobic column not with water but with a water/ethylene glycol mixture. The yield is comparable with that of Example 8a.

For the later operation, the synthetase is therefore preferably eluted solely with water.

d) Scale-up of the hydrophobic interaction chromatography

Test: Purification of the synthetase by HIC. Sample: PEG-1550-containing upper phase with the synthetase. Matrix: phenyl-Sepharose CL-4B. Capacity: 15–20 mg of HSA/ml of gel. Column: 113 mm diameter×16 cm bed height=approx. 1.521 liters gel bed. Flow rate: 7.72 ml/min. Buffer A: 50 mM $Na_2HPO_4$+1.5M $(NH_4)_2SO_4$, pH 7.0. Buffer B: 50 mM $Na_2HPO_4$, pH 7.0. Gradient: 0–100% B in 8 h, linear gradient. Detection: UV absorption at 280 nm.

The procedure here is also as in Example 8a, but the flow rate is higher. 140 U of synthetase from 200 ml of the upper phase with a protein concentration of 15.58 mg/ml are purified with a 95% recovery rate. The packing quality of the column is tested in this case and is 2817 N/m (theoretical layers per square meter).

EXAMPLE 9

Continuous Synthesis of CMP-Neu5Ac from CTP and Neu5Ac in an Enzyme Membrane Reactor The synthesis of CMP-Neu5Ac from CTP and Neu5Ac can be carried out continuously in an enzyme membrane reactor (EMR) with an ultrafiltration membrane having a separation limit of less than or equal to 30000 Daltons, which contains the CMP-Neu5Ac synthetase, into which the reactants CTP and Neu5Ac are fed and from the outflow of which CMP-Neu5Ac is isolated and purified.

The enzymes can be used in soluble form in the EMR since they are held back there by the ultrafiltration membrane, whilst the low-molecular-weight product and unreacted reactants pass through unhindered. The reactor is sterilised before the beginning of the operation, so that the addition of antibacterial substances can be dispensed with. The reactant-containing solution is sterile-filtered into the reactor through a microfilter.

The feed is of the following composition:

| | |
|---|---|
| tris/HCl-buffer, pH 8 | 100 mM |
| $MgCl_2$ | 15 mM |
| Neu5Ac | 10 mM |
| CTP | 10 mM |

A pH value of 8 is established using dilute sodium hydroxide solution. The feed solution is stored cold in an ice-bath.

A synthetase preparation purified by HIC (see Example 8) is used as catalyst in a final concentration of 1U synthetase/ml of reactor volume.

The following operating conditions are observed during the 24-hour test:

| | |
|---|---|
| temperature | 25° C. |
| reactor volume | 10 ml |
| residence time | 1 h |

A CMP-Neu5Ac concentration of 6 mM is measured in the reactor outflow. The CMP-Neu5Ac formed is purified as described in Example 6f by means of diafiltration, anion exchange chromatography and gel chromatography.

EXAMPLE 10

Continuous Synthesis of CMP-Neu5Ac from CTP and Neu5Ac in an Enzyme Membrane Reactor with pH Regulation Apart from the changes below, the procedure is as described in Example 9:

A commercial pH-stat is used to regulate the pH value in the reactor. The actual value is measured in the outflow by means of a throughflow electrode directly behind the ultra-filtration membrane of the reactor. The corrector solution (1N NaOH) is fed to the inlet directly in front of the sterile filter. When constructing the apparatus the dead spaces between the sterile filter and the reactor and between the reactor and the pH throughflow electrode must be kept as small as possible.

A CMP-Neu5Ac concentration of 7.52 mM is measured in the reactor outflow, which corresponds to a conversion of 75% and a space-time yield of 111 g/l of reactor volume/day. The CMP-Neu5Ac formed is purified as described in Example 6f by means of diafiltration, anion exchange chromatography and gel chromatography.

EXAMPLE 11

Selection and Characterisation of a Mutant (CS1) of *E. coli* K-235 with Increased Activity a) Production of the mutant CS1

Biomass of *E. coli* K-235 (ATCC 13027)is spread on a commercial Plate Count Agar (1.0 g/l glucose, 5.0 g/l tryprone, 2.5 g/l yeast extract, pH value approx. 7), supplemented with 7 g/l agar, by means of an inoculating loop for separating the cells. The plates are first of all incubated for 24 h at 37° C. and then for 2–4 weeks at room temperature. After this time the colonies begin to grow in large areas and to slime. Non-slimey cell material, which grows out laterally at the edge of slimey colonies, is removed and is made into a pure culture in customary manner by cell separation by means of spreading.

The colony morphology of the so-obtained CS1 strain differs from that of the starting organism K-235 as follows:

After growth at 37° C. and then at 28° C., in each case for 24 h, the colonies of the new cell line appear slightly transparent in transmitted light and have an irregularly jagged margin. The colonies of the original culture, on the other hand, are not transparent, are slightly thicker, more yellowish and have a smooth margin.

on longer incubation, for example longer than about a week at 28° C., the new culture does not form any slimey colonies.

b) Production of CMP-Neu5Ac synthetase using strain CS1 and *E. coli* K-235 in a complex medium and in a mineral salt medium For further characterisation of the new CS1 strain the growth and the CMP-Neu5Ac synthetase activity are measured in comparison with the original strain in a shake culture. The cultivation is carried out in yeast extract/sorbitol medium (see Example 2a) with 10 g/l of sorbitol, and in the following mineral salt medium:

| | |
|---|---|
| sorbitol | 10.0 g/l |
| $KH_2PO_4$ | 7.81 g/l |
| $(NH_4)_2HPO_4$ | 2.33 g/l |
| $CaCl_2 \times 2H_2O$ | 0.03 g/l |
| $MgSO_4 \times 7H_2O$ (solution (392 g/l)) | 10.0 ml/l |
| thiamine hydrochloride solution (2.67 g/l) | 1.0 ml/l |
| trace element solution | 10.0 ml/l |
| $Fe^{III}$ citrate solution, (0.75 g/l) | 50.0 ml/l |
| pH value | 6.5 |

The composition of the trace element solution is:

| | |
|---|---|
| $CoCl_2 \times 6H_2O$ | 0.267 g/l |
| $MnCl_2 \times 4H_2O$ | 1.6 g/l |
| $CuCl_2 \times 2H_2O$ | 0.151 g/l |
| $H_3BO_3$ | 0.333 g/l |
| $Na_2MoO_4 \times 2H_2O$ | 0.267 g/l |
| $ZnSO_4 \times 7H_2O$ | 1.093 g/l |

The sorbitol, $KH_2PO_4$, $(NH_4)_2HPO_4$ and $CaCl_2 \times 2H_2O$ are mixed in 93 % of the final volume. After autoclaving the salt-containing solutions these are combined under sterile conditions. The thiamine solution is added sterile-filtered. The remainder of the procedure is as indicated in Example 1a.

As Table 7 shows, both organisms grow both on the mineral salt medium and on the complex medium each at the same cell density. The enzyme activity of strain CS1 is distinctly higher in both media than that of *E. coli* K-235.

TABLE 7

Comparison of the growth and the enzyme production of variants CS1 and *E. coli* K-235 in a complex medium and in a mineral salt medium

| | Microorganism | | | | | |
|---|---|---|---|---|---|---|
| | *E. coli* K-235 | | | Strain CS1 | | |
| Medium | cell density ($OD^{660}$) | spec. activity (mU/ mg) | yield/ volume (U/l) | cell density ($OD^{660}$) | spec. activity (mU/ mg) | yield/ volume (U/l) |
| sorbitol/ yeast extract | 5.45 | 17.3 | 9.48 | 5.51 | 26.7 | 13.1 |
| sorbitol/ mineral salts | 3.58 | 16.9 | 7.21 | 3.56 | 32.9 | 12.9 | b) The influence of various carbon sources on the growth of the *E. coli* strains CS1 and K-235 and on the production of CMP-Neu5Ac synthetase The influence of various carbon sources in a concentration of 10 g/l on the growth and the CMP-Neu5Ac synthetase activity is tested as described in Example 1. The basic medium used is the nutrient solution employed in accordance with Example 2a for the fermentation (main difference from Example 1a: 2.5 instead of 0.5 g/l yeast extract and pH 6.5 instead of 7.8).

It can be seen from Table 8 that the strains CS1 and K-235 have the same spectrum as regards the use of carbon sources. High enzyme yields are obtained especially with sorbitol and sodium acetate.

TABLE 8

Comparison of the growth and of the enzyme production of strains CS1 and E. coli K-235 in the presence of various carbon sources

| | Microorganism | | | | | |
|---|---|---|---|---|---|---|
| | E. coli K-235 | | | Strain CS1 | | |
| C source | cell density ($OD^{660}$) | spec. activity (mU/mg) | yield/volume (U/l) | cell density ($OD^{660}$) | spec. activity (mU/mg) | yield/volume (U/l) |
| xylose | 5.72 | 7.0 | 2.92 | 6.14 | 14.8 | 8.61 |
| sorbitol | 5.74 | 17.7 | 7.93 | 5.65 | 27.2 | 13.5 |
| sodium succinate | 2.28 | 5.6 | 1.82 | 2.5 | 8.0 | 2.96 |
| saccharose | 1.36 | 1.5 | 0.34 | 1.34 | 3.6 | 0.87 |
| sodium acetate | 3.27 | 23.7 | 9.50 | 3.59 | 43.8 | 16.8 |
| malic acid | 2.7 | 10.7 | 3.17 | 2.6 | 23.0 | 7.67 |
| lactic acid | 3.7 | 28.0 | 10.6 | 3.6 | 38.7 | 15.8 | n.d.: not determined

EXAMPLE 12

Fermentative Production of Biomass of Cell Variant CS1

For the fermentative production of biomass of strain CS1 the procedure is essentially in accordance with Example 2 b), but with the following modifications:

A 19 l bioreactor containing 7 l is used.

Sorbitol and yeast extract are led in subsequently in 21 portions each of 140 ml. The composition of the first 13 portions is: 300 g/l of sorbitol, 125 g/l of yeast extract, 11 g/l of $K_2HPO_4$, 2.5 g/l of $(NH_4)_2SO_4$, 30 mg/l of $CaCl_2$. For the remaining additions sorbitol and yeast extract are dissolved in the above-mentioned concentration in deionised water.

At a cell density of $OD^{660}=88$ $K_2HPO_4$ is added to the fermentation broth to a final concentration of 1.5 g/l.

At the time of the maximum $OD^{660}$ (=94.0), a moist biomass content of 314 g/l (dry mass=50.9 g/l) and an enzyme yield/volume of 191 U/l of fermentation broth with a specific activity of 28.0 mU/mg are achieved.

The strain E. coli K-235/CS1 can be used instead of the strain E. coli K-235 for the production of cell extracts having CMP-Neu5Ac synthetase activity, which in turn can be used in accordance with the invention for the production of CMP-activated sialic acids, analogously to the preceding Examples.

Deposit of microorganisms

The strain E.coli K-235/CS1 was deposited at the Deutsche Sammlung yon Mikroorganismen (DSM), Mascheroder Weg 1b, D-3300 Braunschweig, on Jun. 18, 1992 under the deposit number DSM 7114.

The strain E. coli K-235 (ATCC 13027) is available through the American Type Culture Collection in Rockville, Md. under the accession number ATCC 13027.

What is claimed is:

1. A process for the preparation of a cytidine 5'-monophosphosialic acid which comprises obtaining a cell extract by cultivating a naturally occurring microorganism having cytidine 5'-monophospho-N-acetylneuraminic acid synthetase activity, breaking down the microorganism, and removing the insoluble cell components; and continuously reacting a sialic acid with cytidine 5'-triphosphate in the presence of the cell extract in an enzyme membrane reactor, the extract optionally having been subjected to one purification step.

2. A process for the preparation of a cytidine 5'-monophospho(CMP)-sialic acid according to claim 1, wherein the sialic acid is selected from the group N-acetylneuraminic acid (Neu5Ac), N-acetyl-4-O-acetylneuraminic acid (Neu4,5Ac2), N-acetyl-9-O-acetylneuraminic acid (Neu5,9Ac2), N-acetyl-7,9-di-O-acetylneuraminic acid (Neu5,7,9Ac3), N-acetyl-8,9-di-O-acetylneuraminic acid (Neu5,8,9Ac3), N-acetyl-9-O-lactoylneuraminic acid (Neu4Ac9Lt), N-acetyl-4-O-acetyl-9-O-lactoylneuraminic acid (Neu4,5Ac29Lt), N-acetylneuraminic acid 9-phosphate (Neu5Ac9P), N-glycoloylneuraminic acid (Neu5Gc), N-glycoloyl-9-O-acetylneuraminic acid (Neu9Ac5Gc), N-glycoloyl-9-O-lactoylneuraminic acid (Neu5Gc9Lt), N-glycoloylneuraminic acid 8-sulfate (Neu5Gc8S), 5-azidoneuraminic acid, N-acetyl-9-azido-9-deoxy-neuraminic acid and N-acetyl-9-acetamido-9-deoxy-neuraminic acid.

3. A process for the preparation of a cytidine 5'-monophospho(CMP)-sialic acid according to claim 1, wherein the sialic acid is selected from the group Neu4,5Ac2, Neu5,9Ac2, Neu5Gc, Neu9Ac5Gc, N-acetyl-9-deoxy-neuraminic acid, N-acetyl-9-azido-9-deoxy-neuraminic acid, 5-azidoneuraminic acid and Neu5Ac.

4. A process according to claim 1, wherein the sialic acid is prepared in situ in the reaction mixture from suitable precursors.

5. A process according to claim 1, wherein cytidine 5'-triphosphate (CTP) is prepared in situ in the reaction mixture from suitable precursors.

6. A process according to claim 1, wherein the microorganism is selected from the group Escherichia coli serotype K1, a species of Streptococcus serotype B or C, Neisseria meningitidis, Pasteurella haemolytica, Pasteurella multacida, Moraxella nonliquefaciens, Citrobacter freundii, a Salmonella species, e.g. S. dahlem, S. djakarta or S. trouca, Actinomyces viscosus and Corynebacterium parvum.

7. A process according to claim 6, wherein the microorganism is an E. coli strain of the serotype K1.

8. A process according to claim 7, wherein the microorganism is E. coli K-235 (ATCC 13027).

9. A process according to claim 7, wherein the microorganism is E. coli K-235/CS1 (DSM 7114).

10. A process according to claim 1, wherein the cell extract is subjected to one purification step selected from precipitation with polyethylene glycol, anion exchange chromatography, hydrophobic interaction chromatography, gel filtration, affinity chromatography, chromatography on hydroxy apatite and chromatofocussing.

11. A process according to claim 10, wherein the cell extract is purified by means of hydrophobic interaction chromatography.

12. A process according to claim 1, wherein the reaction is carried out in homogeneous aqueous solution at 20°–35° C. in the presence of approximately 10–50 mM $Mg^{2+}$ or in the presence of approximately 5–30 mM $Mn^{2+}$, the pH value of the reaction being approximately 8–11 in the presence of $Mg^{2+}$ ions and approximately 6–8 in the presence of $Mn^{2+}$ ions.

13. A process according to claim 10, wherein the purification step comprises protein precipitation with polyethylene glycol.

14. A process for the preparation of CMP-Neu5Ac according to claim 1, wherein the reaction of Neu5Ac with CTP is carried out continuously in an enzyme membrane reactor that contains the cell extract, into which the reactants Neu5Ac and CTP are fed and from the outflow of which CMP-Neu5Ac is isolated.

15. The process of claim 1, wherein the insoluble cell components are removed using an aqueous two-phase system.

* * * * *

UNITED STATES PATENT AND TRADEMARK OFFICE
CERTIFICATE OF CORRECTION

PATENT NO. : 5,334,514
DATED : August 2, 1994
INVENTOR(S) : Kittelmann, et al

It is certified that error appears in the above-indentified patent and that said Letters Patent is hereby corrected as shown below:

Column 24, line 24 change "N-acetyl-9-" to
-- N-acetyl-9-acetamido-9- --

Signed and Sealed this

Twenty-seventh Day of September, 1994

Attest:

BRUCE LEHMAN

*Attesting Officer*     *Commissioner of Patents and Trademarks*